(12) United States Patent
Li et al.

(10) Patent No.: US 11,260,031 B2
(45) Date of Patent: Mar. 1, 2022

(54) PROTEIN PARTICLE WITH A POORLY WATER-SOLUBLE DRUG ENCAPSULATED THEREIN AND PREPARATION METHOD THEREOF

(71) Applicant: ACADEMY OF MILITARY MEDICAL SCIENCES, Beijing (CN)

(72) Inventors: Zhiping Li, Beijing (CN); Zhenbo Yang, Beijing (CN); Yang Yang, Beijing (CN); Fanglin Yu, Beijing (CN); Wei Gong, Beijing (CN); Meiyan Yang, Beijing (CN); Yuli Wang, Beijing (CN); Chunsheng Gao, Beijing (CN); Xingguo Mei, Beijing (CN)

(73) Assignee: ACADEMY OF MILITARY MEDICAL SCIENCES, Beijing (CN)

( * ) Notice: Subject to any disclaimer, the term of this patent is extended or adjusted under 35 U.S.C. 154(b) by 0 days.

(21) Appl. No.: 16/608,638

(22) PCT Filed: Apr. 26, 2018

(86) PCT No.: PCT/CN2018/084654
§ 371 (c)(1),
(2) Date: Oct. 25, 2019

(87) PCT Pub. No.: WO2018/196819
PCT Pub. Date: Jan. 11, 2018

(65) Prior Publication Data
US 2020/0197314 A1   Jun. 25, 2020

(30) Foreign Application Priority Data
Apr. 28, 2017   (CN) .......................... 201710290102.5

(51) Int. Cl.
*A61K 9/48*     (2006.01)
*A61K 9/14*     (2006.01)

(52) U.S. Cl.
CPC ............ *A61K 9/4833* (2013.01); *A61K 9/145* (2013.01); *A61K 9/4825* (2013.01)

(58) Field of Classification Search
None
See application file for complete search history.

(56) References Cited

U.S. PATENT DOCUMENTS

| 4,842,856 A | 6/1989 | Hoederath et al. |
| 5,916,596 A | 6/1999 | Desai et al. |
| 6,749,868 B1 | 6/2004 | Desai et al. |
| 2009/0104291 A1 | 4/2009 | Kanazawa |

FOREIGN PATENT DOCUMENTS

| CN | 1237901 | 12/1999 |
| CN | 102232933 | 11/2011 |
| CN | 102327230 | 1/2012 |
| CN | 102357076 | 2/2012 |
| CN | 102357077 | 2/2012 |
| CN | 105816885 | 8/2016 |
| CN | 107412783 | 12/2017 |
| JP | 2009-96787 | 5/2009 |
| JP | 2009-185042 | 8/2009 |
| WO | WO 1998/14174 | 4/1998 |
| WO | WO 2014/197640 A1 | 12/2014 |
| WO | WO 2018/196819 A1 | 11/2018 |

OTHER PUBLICATIONS

Written Opinion received in in PCT Application No. PCT/CN2018/084654 dated Jun. 27, 2018 (in Chinese and English translation thereof).
International Search Report received in PCT Application No. PCT/CN2018/084654 dated Jun. 27, 2018 (in Chinese and English translation).
Written Opinion received in in PCT Application No. PCT/CN2018/084654 dated Jun. 27, 2018 (in Chinese).

*Primary Examiner* — Robert A Wax
*Assistant Examiner* — Randeep Singh
(74) *Attorney, Agent, or Firm* — Crowell & Moring LLP

(57) ABSTRACT

The present invention relates to a protein particle with a poorly water-soluble drug encapsulated therein and a preparation method therefor. The preparation method comprises the following steps: i) dissolving a poorly water-soluble drug and a liquid solubilizer into a good solvent; ii) partially or fully removing said good solvent from the product of step i); iii) mixing the product of step ii) with a protein; and iv) dispersing the product of step iii) in a poor solvent. The preparation method is simple and is suitable for industrial production.

13 Claims, 8 Drawing Sheets

PROTEIN PARTICLE WITH A POORLY WATER-SOLUBLE DRUG ENCAPSULATED THEREIN AND PREPARATION METHOD THEREOF

CROSS-REFERENCE TO RELATED APPLICATIONS

The present application is a § 371 national phase application of International Application No. PCT/CN2018/084654, filed Apr. 26, 2018, which claims priority to Chinese Patent Application No. 201710290102.5, filed Apr. 28, 2017, contents of which are incorporated by reference in their entirety.

TECHNICAL FIELD

The disclosure belongs to the field of pharmacy, specifically relates to a protein particle with a poorly water-soluble drug encapsulated therein and preparation method thereof.

BACKGROUND ART

A nano-transport system for drugs denotes nano-particles formed by encapsulating a drug with a material. Research has found that encapsulating a drug in a nano-transport system can result in change of the drug's in vivo behaviors such as release, distribution and metabolism. By surface modification, specific uptake in target tissues and target cells, specific binding and accumulating can be realized, thereby improving the therapeutic effect of drugs, and reducing side effects caused by systemically administered drugs, which can improve the compliance of patients. Therefore, nano-transport carrier provides a new path for obtaining a better therapeutic effect of drugs.

Albumin nano-particle is one of the nano-transport systems that get the most attention. Because albumin is an endogenous substance, it is of characteristics of non-toxicity, no immunogenicity, bio-degradability and good biocompatibility. Therefore, albumin is an ideal natural drug carrier.

SUMMARY OF THE INVENTION

An object of the disclosure is to provide a protein particle with a poorly water-soluble drug encapsulated therein and a preparation method thereof.

In the first aspect of the disclosure, it is provided a method for preparing a protein particle with a poorly water-soluble drug encapsulated therein, comprising the following steps:
i) dissolving a poorly water-soluble drug and a liquid solubilizer in a good solvent;
ii) partially or fully removing said good solvent from the product of step i);
iii) mixing the product of step ii) with a protein;
iv) dispersing the product of step iii) in a poor solvent.

In some embodiments, the method according to any aspect of the disclosure comprises the following steps:
i) dissolving a poorly water-soluble drug and a liquid solubilizer in a good solvent for the poorly waters-soluble drug;
ii) partially or fully removing said good solvent for the poorly water-soluble drug from the product of step i);
iii) mixing the product of step ii) with a protein;
iv) dispersing the product of step iii) in a poor solvent for the poorly water-soluble drug, obtaining a protein particle with a poorly water-soluble drug encapsulated therein.

In some embodiments, the method according to any aspect of the disclosure is performed at a temperature of less than or equal to 45° C., preferably at a temperature of less than or equal to 40° C., preferably at a temperature of less than or equal to 35° C., still preferably at a temperature of less than or equal to 30° C.

In some embodiments, the product of step i) is a liquid (for example a transparent solution).

In some embodiments, the product of step ii) is a liquid (for example a transparent solution).

In some embodiments, the poorly water-soluble drug exists as a form of solution in the product of step ii).

In some embodiments, said liquid solubilizer comprises: one or more selected from the group consisting of propanol (e.g. isopropanol), liquid polyethylene glycol (e.g. one or more selected from the group consisting of polyethylene glycol 200, polyethylene glycol 400, polyethylene glycol 600 or polyethylene glycol 800), Tween (e.g. Tween 20 or Tween 80), Span and glycerol.

In some embodiments, said liquid solubilizer comprises: liquid polyethylene glycol (for example one or more selected from the group consisting of polyethylene glycol 200, polyethylene glycol 400, polyethylene glycol 600 or polyethylene glycol 800) or Tween (for example Tween20 or Tween80).

In some embodiments, said good solvent for the poorly water-soluble drug comprises one or more selected from the group consisting of ethanol, methanol, diethyl ether, dichloromethane and chloroform.

In some embodiments, said good solvent for the poorly water-soluble drug comprises ethanol.

In some embodiments, said poor solvent for the poorly water-soluble drug comprises water.

In some embodiments, said poor solvent for the poorly water-soluble drug comprises physiologically acceptable aqueous solution.

In some embodiments, said poor solvent for the poorly water-soluble drug comprises buffer solution.

In some embodiments, said poor solvent for the poorly water-soluble drug comprises aqueous solution of salt and/or sugar.

In some embodiments, step ii) comprises: partially or fully removing said good solvent for the poorly water-soluble drug from the product of step i) by one or more operations selected from the group consisting of rotating evaporation, heating and vacuum pumping.

In some embodiments, the good solvent for the poorly water-soluble drug is present at a content of less than or equal to 1 wt % in the product of step ii).

In some embodiments, in step iii), said protein is in powder form.

In some embodiments, said protein is albumin.

In some embodiments, said albumin comprises one or more selected from the group consisting of recombinant albumin, natural albumin and modified albumin.

In some embodiments, step iv) comprises: dispersing the product of step iii) in a poor solvent by one or more operations selected from the group consisting of stirring, shearing, ultrasonic treatment, homogenizing, grinding etc.

In some embodiments, the method according to any aspect of the disclosure further comprises the following step: removing the liquid solubilizer from the product of step iv).

In some embodiments, one or more operations selected from the group consisting of dialysis, gel filtration, elution through microcolumn are employed for removing the liquid solubilizer from the product of step iv).

In some embodiments, the method according to any aspect further comprises the following step: separating an albumin particle from the product of step iv).

In some embodiments, one or more operations selected from the group consisting of centrifugation, filtration and drying (e.g. freeze drying) are employed for separating an albumin particle from the product of step iv).

In some embodiments, said poorly water-soluble drug comprises one or more selected from the group consisting of paclitaxel, docetaxel, camptothecin, hydroxycamptothecin, rapamycin, doxorubicin, itraconazole, nimodipine.

In some embodiments, the protein particles (protein nanoparticles) have an average particle size of 100~1000 nm, for example 200~2000 nm, still for example 150~250 nm.

In some embodiments, the protein particles (protein nanoparticles) have an average particle size of 50~100 nm, 100~150 nm, 150~200 nm, 200~250 nm, 250~30 nm, 300~350 nm, 350~400 nm, 400~450 nm, 450~500 nm, 500~600 nm, 600~700 nm, 700~800 nm, 800~900 nm or 900~1000 nm.

A second aspect of the disclosure provides a protein particle with a poorly water-soluble drug encapsulated therein, which is prepared by the method according to any aspect of the disclosure.

In some embodiments, 1 g (ml) of poorly water-soluble drug is capable of being dissolved in less than 30 ml of good solvent for the poorly water-soluble drug.

In some embodiments, 1 g (ml) of poorly water-soluble drug is incapable of being completely dissolved in less than 30 ml of poor solvent for the poorly water-soluble drug.

In some embodiments, the liquid solubilizer refers to a liquid substance which can improve the solubility of the poorly water-soluble drug.

In some embodiments, the liquid solubilizer is water soluble.

In some embodiments, the good solvent for the poorly water-soluble drug refers to a solvent, which is capable of dissolving the poorly water-soluble drug effectively.

In some embodiments, the poor solvent for the poorly water-soluble drug is an aqueous medium.

In some embodiments, said poorly water-soluble drug has hydroxyl, other active groups or hydrophobic groups, which result in a covalent or non-covalent interaction between the albumin and the drug, and the albumin being adhered to the surface of the drug.

In some embodiments, said poorly water-soluble drug has hydroxyl, other active groups or hydrophobic groups, which result in a covalent or non-covalent interaction between the albumin and the drug.

In some embodiments, said albumin is human-derived albumin.

In some embodiments, said albumin is an albumin which is derived from other species, and has been modified to avoid triggering an immune response of an organism.

In some embodiments, the poor solvent for the poorly water-soluble drug is a solution system which is capable of improving properties of drug delivery systems, including body's tolerance or the stability, etc.

In some embodiments, poor solvent for the poorly water-soluble drug may comprise water, buffer solution, salt solution, sugar solution or physiologically acceptable solution.

In some embodiments, buffer solution may be phosphate buffer solution, citric acid buffer solution, acetate buffer solution, etc.

In some embodiments, the salt solution may be sodium chloride solution.

In some embodiments, the sugar solution may be glucose solution, lactose solution or mannitol solution, etc.

In some embodiments, the physiologically acceptable solution is a solution which is tolerated by an organism when administrated orally, by injection, by inhalation or topically.

In some embodiments, poor solvent for the poorly water-soluble drug may contain osmotic pressure regulator, pH regulator, freeze-drying protectant, suspension aid, stabilizer, etc.

In some embodiments, the product of step i), ii) or iii) does not comprise poor solvent for the poorly water-soluble drug, for example does not comprises water.

In some embodiments, the method according to any aspect of the disclosure comprises a step of modifying the protein particle with a poorly water-soluble drug encapsulated therein.

In some embodiments, the protein particle with a poorly water-soluble drug encapsulated therein may be modified with materials such as polymer polyethylene glycol (for example polyethylene glycol 2000 or polyethylene glycol 4000), polymer polyethylene glycol for targeting modification, etc., thereby functions like long circulating or long-circulating targeted deliver can be obtained.

In some embodiments, the protein particle with a poorly water-soluble drug encapsulated therein has a size of 100~1000 nm, for example 150~250 nm, still for example 170~210 nm, still for example 140~160 nm, still for example 186 nm, 173 nm, 192 nm, 204 nm or 193 nm.

In some embodiments, any method according to the disclosure comprises dissolving a poorly soluble drug and a liquid solubilizer in the presence of a good solvent (for example ethanol) firstly, then removing the good solvent to form a liquid complex of the poorly soluble drug and the liquid solubilizer, wherein the poorly soluble drug exists in the solution; then mixing the liquid complex with protein powder, dispersing them into a poor solvent, wherein the poorly soluble drug is separated out and encapsulated by protein, and nano-particles are formed. This method may be performed without using high temperature, which is beneficial for improving the stability of the drug.

In some embodiments, in step i), the mass ratio of poorly water-soluble drug to the protein in step iii) is 1:0.1~15, for example 1:0.1~0.5, for example 1:0.5~1, for example 1:1~2, for example 1:2~3, for example 1:3~4, for example 1:4~5, for example 1:5~6, for example 1:6~8, for example 1:8~10, for example 1:10~15.

In some embodiments, in step i), the mass/volume ratio of poorly water-soluble drug to liquid solubilizer is 0.1 g:0.01~10 ml, for example 0.1 g:0.01~0.1 ml, for example 0.1 g:0.1~0.4 ml, for example 0.1 g:0.4~1 ml, for example 0.1 g:1~2 ml, for example 0.1 g:2~3 ml, for example 0.1 g:3~5 ml, for example 0.1 g:5~10 ml.

In some embodiments, in step iii), the mass/volume ratio of the poorly water-soluble drug to the poor solvent is 0.1 g:1~100 ml, for example 0.1 g:1~2 ml, 0.1 g:2~4 ml, 0.1 g:4~6 ml, 0.1 g:6~8 ml, 0.1 g:8~10 ml, 0.1 g:10~15 ml, 0.1 g:15~20 ml, 0.1 g:20~50 ml or 0.1 g:50~100 ml.

In some embodiments, the poor solvent for the poorly water-soluble drug is a buffer solution.

In some embodiments, the buffer solution is a citric acid buffer solution or a PBS buffer solution.

In some embodiments, the poor solvent for the poorly water-soluble drug has a pH of 5~8, for example a PH of 5~6, 6~7 or 7~8, for example a pH of 7.4.

In some embodiments, any method according to the disclosure comprises dissolving a poorly soluble drug and a liquid solubilizer in the presence of a good solvent (for example ethanol) firstly, then removing the good solvent to form a liquid complex of the poorly soluble drug and the liquid solubilizer, wherein the poorly soluble drug exists in the solution; then mixing the liquid complex with protein powder, dispersing the mixed product into a poor solvent, wherein the poorly soluble drug is separated out and encapsulated by protein, and nano-particles are formed. This method may be performed without using high temperature, which is beneficial for the stability of the drug.

In some embodiments, the poor solvent refers to a poor solvent for the poorly water-soluble drug.

In some embodiments, the good solvent refers to a good solvent for the poorly water-soluble drug.

In some embodiments, 1 g of poorly water-soluble drug is incapable of being completely dissolved in X ml of poor solvent for the poorly water-soluble drug, X≥30, for example X≥100, for example X≥200, for example X≥400, for example X≥600, for example X≥800, for example X≥1000, for example X≥2000, for example X≥3000, for example X≥5000, for example X≥10000.

In some embodiments, 1 g of poorly water-soluble drug is capable of being completely dissolved in Y ml of good solvent for the poorly water-soluble drug, Y≤100, for example Y≤80, for example Y≤60, for example Y≤40, for example Y≤30, for example Y≤15.

In some embodiments, the good solvent for the poorly water-soluble drug is a solvent having a dielectric constant less than or equal to 80, for example a dielectric constant less than 60, for example a dielectric constant less than 40, for example a dielectric constant less than 20, for example a dielectric constant less than 10.

In some embodiments, the poor solvent for the poorly water-soluble drug is a solvent having a dielectric constant more than 80, for example a dielectric constant more than or equal to 90, for example a dielectric constant more than or equal to 100.

In some embodiments, the PBS solution is phosphate buffer solution (phosphate buffer saline). Optionally, PBS solution has a pH of 7.4.

In some embodiments, the suspension is a heterogeneous liquid formed by the poorly water-soluble drug being dispersed in a liquid medium as micro particles.

In some embodiments, the poorly water-soluble drug denotes solid drugs which is poorly soluble in water.

In some embodiments, no crosslinking agent is used in the method of the present disclosure, for example crosslinking agent such as glutaraldehyde etc. is not used.

In some embodiments, the average particle size of the protein particles is measured by a laser particle size analyzer (for example through a laser diffraction method).

In some embodiments, the liquid polyethylene glycol has a molecular weight of 200~800.

In some embodiments, the protein particle with a poorly water-soluble drug encapsulated therein has an encapsulation efficiency of more than or equal to 90%, for example more than or equal to 92%.

In some embodiments, the protein particle with a poorly water-soluble drug encapsulated therein has a drug loading of 5~95%, for example 10~45%, for example 15~35%.

In some embodiments, "encapsulated" means the poorly water-soluble drug is partially or fully encapsulated by protein. For example, in a protein particle with a poorly water-soluble drug encapsulated therein, there may be some poorly water-soluble drug fully encapsulated by the protein, or there may be some poorly water-soluble drug partially encapsulated by the protein. Optionally, the surface of the protein particle with a poorly water-soluble drug encapsulated therein is fully covered by protein. Optionally, the protein particle with a poorly water-soluble drug encapsulated therein is partially covered by protein, which means, there is exposed poorly water-soluble drug on the surface of the particle.

The disclosure further provides a pharmaceutical composition, which comprises any protein particle with a poorly water-soluble drug encapsulated therein according to the disclosure and a pharmaceutically acceptable excipient.

BENEFICIAL EFFECTS OF THE DISCLOSURE

One or more examples have one or more of the following beneficial effects:
i) preparation process is relatively simple;
ii) key processes are easy to control;
iii) stable protein particle can be obtained without the need of solidification of albumin;
iv) by this method, drug loading and/or encapsulation efficiency for the protein particles with a poorly water-soluble drug encapsulated therein produced are relatively high;
v) it is easy to control the particle size of the protein particles with a poorly water-soluble drug encapsulated therein;
vi) the method of dissolving active ingredient is by co-dissolving active ingredient and solubilizer into an organic solvent, and then removing organic solvent, forming a complex of active ingredient and solubilizer, wherein the solubility of the active ingredient is significantly improved in the complex, even better than the solubilization effect brought by the organic solvent;
vii) in the preparation process of the protein particle with a poorly water-soluble drug encapsulated therein, the protein particle is obtained in one step by stirring, shearing, ultrasonic treatment, homogenizing, grinding, etc., without producing oil-in-water emulsion or a water-in-oil emulsion. The organic solvent can be easily completely removed;
viii) No high temperature treatment is involved during the preparation process, which is beneficial for the stability of the drug.

DESCRIPTION OF FIGURES

The drawings described herein are provided for a further understanding of the present disclosure and are intended to be a part of the present disclosure, however, the illustrative examples of the disclosure and the description thereof are used for explaining the present disclosure and are not intended to limit the disclosure. In the figures.

EXAMPLES

Figure 1:
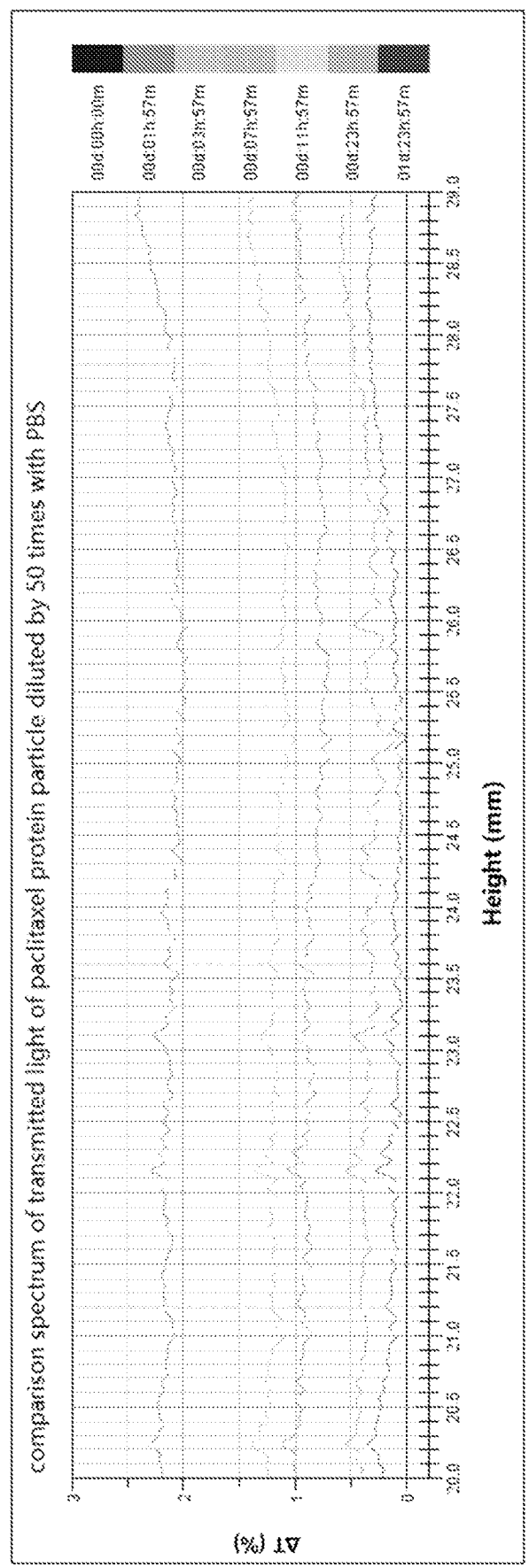
FIG. 1 depicts curves reflecting intensity variation of transmitted light of paclitaxel protein particle diluted by 50 times with PBS.

The embodiments of the disclosure are specifically described by the following figures and examples.

Instruments used in the following examples are shown in the following table:

| Name of Instruments | Manufacture and Brands |
|---|---|
| Rotary Evaporator | RE-2000, Shanghai Yarong Biochemical Instrument Factory |
| Circulating Water Vacuum Pump | SHD-D(III), Gongyi City Yingyu Yuhua Instrument Factory |
| High Performance Liquid Chromatography | degasser G1379B; Bin Pump SL G1312B, Hip-ALSSL G1367C, TCCSL G1316B, UV G1314C, U.S. Agilent Company; chromatographic column (Agilent Eclipse plus-$C_8$ 4.6 × 250 mm 5 µm, U.S. Agilent Company) |
| Ultrasonic Cell Disruptor | SCIENTZ (IID), Ningbo Scientz Biotechnology Co,. LTD |
| High-pressure Homogenizer | AVESTIN, Canada, EmulsiFlex-C3 |
| Stability Meter | Formulation TURBISCAN TOWER |
| Particle Size Meter | FLUOSTAR, Germany Symptec |
| Centrifugal Equipment | Micromax, U.S. |
| Human Serum Albumin | Batch Number: VNA1Q087, Baxter AG (U.S. Baxter Company) |

Example 1

50 mg of paclitaxel was weighed, added with 400 µL of PEG600, added with 10 mL of anhydrous ethanol, and the mixture was subjected to ultrasonic treatment (with a water temperature of 30–45° C.) until it became transparent, ethanol was removed by rotary evaporation under reduced pressure, and a paclitaxel-polyethylene glycol complex was formed with a residual amount of ethanol of less than or equal to 0.5 wt %;

100 mg of human serum albumin powder was weighed and added to the paclitaxel-polyethylene glycol complex, mixed well, to obtain a mixture.

The abovementioned mixture was added to 2 mL of PBS solution with a pH of 7.4, and the mixture was subjected to ultrasonic treatment in an ultrasonic disruptor with 45% of total power for 200 s (ultrasonic treatment for 2 s—pausing for 2 s, in a loop), to obtain a suspension.

The suspension was put into a dialysis bag containing a PBS solution having a pH of 7.4, and repeatedly dialyzed to remove PEG600 and free albumin. Subsequently, the suspension was subjected to configuration with a speed of 3000 rpm for 10 min to remove drug participants that were not encapsulated, then the product was subjected to freeze drying, to obtain protein particles with paclitaxel encapsulated therein.

Example 2

100 mg of 10-hydroxycamptothecin was weighed, added with 1 mL of PEG400, added with a appropriate amount of anhydrous ethanol, and the mixture was subjected to ultrasonic treatment until it became transparent, ethanol was removed by rotary evaporation under reduced pressure, and a 10-hydroxycamptothecin-polyethylene glycol complex was formed with a residual amount of ethanol of less than or equal to 0.5 wt %;

300 mg of human serum albumin powder was weighed and added to the complex, mixed well, to obtain a mixture.

The abovementioned mixture is added into 10 mL of citric acid buffer solution having a pH of 5.0, the mixture was homogenized by passing through a membrane using a high-pressure homogenizer, to obtain a suspension.

The suspension was put into a dialysis bag and repeatedly dialyzed to remove PEG400 and free albumin.

The suspension was subjected to centrifugation with a speed of 3000 rpm for 10 min to remove drug participants that were not encapsulated, then the product was subjected to freeze drying, to obtain protein particles with 10-hydroxycamptothecin encapsulated therein.

Example 3

Approximately 100 mg of docetaxel was weighed, added with 500 µL of PEG400, added with an appropriate amount of anhydrous methanol, and the mixture was subjected to ultrasonic treatment until it became transparent, methanol was removed by rotary evaporation under reduced pressure, and a docetaxel-polyethylene glycol complex was formed with a residual amount of ethanol of less than or equal to 0.5 wt %;

300 mg of human serum albumin powder was weighed and added to the complex, mixed well, to obtain a mixture.

The abovementioned mixture is added into 10 mL of citric acid buffer solution having a pH of 5.0, and the mixture was homogenized by passing through a membrane using a high-pressure homogenizer, to obtain a suspension.

The suspension was put into a dialysis bag and repeatedly dialyzed to remove PEG400 and free albumin. The suspension was subjected to centrifugation with a speed of 3000 rpm for 10 min to remove drug participants that were not encapsulated, then the product was subjected to freeze drying, to obtain protein particles with docetaxel encapsulated therein.

Example 3b

Approximately 100 mg of docetaxel was weighed, added with 500 µL of PEG400, added with an appropriate amount of anhydrous methanol, the mixture was subjected to ultrasonic treatment until it became transparent, methanol was removed by rotary evaporation under reduced pressure, and a docetaxel-polyethylene glycol complex was formed with a residual amount of ethanol of less than or equal to 0.5 wt %;

300 mg of human serum albumin powder was weighed and added to the complex, mixed well, to obtain a mixture;

The abovementioned mixture was added into 10 mL of PBS solution having a pH of 7.4, and the mixture was homogenized by passing through a membrane using a high-pressure homogenizer, to obtain a suspension.

The suspension was put into a dialysis bag and repeatedly dialyzed to remove PEG400 and free albumin. The suspension was subjected to centrifugation with a speed of 3000 rpm for 10 min to remove drug participants that were not encapsulated, then the product was subjected to freeze drying, to obtain protein particles with docetaxel encapsulated therein.

Example 4

Approximately 100 mg of rapamycin was weighed, added with 1 mL of PEG400, added with an appropriate amount of anhydrous ethanol, and the mixture was subjected to ultrasonic treatment until it became transparent, ethanol was removed by rotary evaporation under reduced pressure, and a rapamycin-polyethylene glycol complex was formed with a residual amount of ethanol of less than or equal to 0.5 wt %.

300 mg of human serum albumin powder was weighed and added to the complex, to obtain a mixture by mixing.

The abovementioned mixture was added into 10 mL of citric acid buffer solution having a pH of 5.0, and the mixture was homogenized by passing through a membrane using a high-pressure homogenizer, to obtain a suspension. The suspension was put into a dialysis bag, and repeatedly dialyzed to remove PEG400 and free albumin.

The suspension was subjected to centrifugation with a speed of 3000 rpm for 10 min to remove drug participants that were not encapsulated, then the product was subjected to freeze drying, to obtain protein particles with rapamycin encapsulated herein.

Example 5

Approximately 100 mg of itraconazole was weighed, added with 1 mL of PEG400, added with an appropriate amount of anhydrous ethanol, and the mixture was subjected to ultrasonic treatment until it became transparent, ethanol was removed by rotary evaporation under reduced pressure, and an itraconazole-polyethylene glycol complex was formed with a residual amount of ethanol of less than or equal to 0.5 wt %;

300 mg of human serum albumin powder was weighed and added to the complex, mixed well, to obtain a mixture.

The abovementioned mixture was added into 10 mL of citric acid buffer solution having a pH of 5.0, and the mixture was homogenized by passing through a membrane using a high-pressure homogenizer, obtaining a suspension.

The suspension was put into a dialysis bag and repeatedly dialyzed to remove PEG400 and free albumin. The suspension was subjected to centrifugation with a speed of 3000 rpm for 10 min to remove drug participants that were not encapsulated, then the product was subjected to freeze drying, to obtain protein particles with itraconazole encapsulated therein.

Example 5b

Approximately 100 mg of itraconazole was weighed, added with 1 mL of PEG400, added with an appropriate amount of anhydrous ethanol, the mixture was subjected to ultrasonic treatment until it became transparent, ethanol was removed by rotary evaporation under reduced pressure, and an itraconazole-polyethylene glycol complex was formed with a residual amount of ethanol of less than or equal to 0.5 wt %;

300 mg of human serum albumin powder was weighed and added to the complex, mixed well, to obtain a mixture.

The abovementioned mixture is added into 10 mL of PBS solution having a pH of 7.4 solution, and the mixture was homogenized by passing through a membrane using a high-pressure homogenizer, obtaining a suspension.

The suspension was put into a dialysis bag and repeatedly dialyzed to remove PEG400 and free albumin. The suspension was subjected to centrifugation with a speed of 3000 rpm for 10 min to remove drug participants that were not encapsulated, then the product was subjected to freeze drying, to obtain protein particles with itraconazole encapsulated therein.

Example 6

Approximately 100 mg of hydroxycamptothecin was weighed, added with 1 mL of Tween80, added with an appropriate amount of anhydrous ethanol, and the mixture was subjected to ultrasonic treatment until it became transparent, ethanol was removed by rotary evaporation under reduced pressure, and a hydroxycamptothecin-Tween80 complex was formed with a residual amount of ethanol of less than or equal to 0.5 wt %;

300 mg of human serum albumin powder was weighed and added to the complex, mixed well, to obtain a mixture.

The abovementioned mixture is added into 10 mL of citric acid buffer solution having a pH of 5.0, and the mixture was homogenized by passing through a membrane using a high-pressure homogenizer, obtaining a suspension.

The suspension was put into a dialysis bag and repeatedly dialyzed to remove Tween80 and free albumin. The suspension was subjected to centrifugation with a speed of 3000 rpm for 10 min to remove drug participants that were not encapsulated, then the product was subjected to freeze drying, to obtain protein particles with hydroxycamptothecin encapsulated therein.

Yields of nearly 100% were achieved by the methods of Example 1~6.

Assay 1—The Measurement of Encapsulation Efficiency and Drug Loading (1) Approximately 10 mg of albumin particles were provided, an appropriate amount of ethanol was added to completely dissolve the albumin particles, and they were diluted with the mobile phase to a certain volume, the concentration of the drug was measured by HPLC method, and the total amount of drug in the particles (A) was calculated.

(2) Another approximately 10 mg of albumin particles were provided, an appropriate amount of water was added, mixed well, and the mixture was centrifuged for 3000 rpm for 10 min. After the centrifugation, if there were any, the precipitates were collected, dissolved with an appropriate amount of ethanol, diluted with mobile phase to a certain volume, and the concentration of the drug was measured by HPLC method, and the total amount of drug in the precipitates (B) was calculated.

After the centrifugation, the upper layer of the suspension was collected and centrifuged with a super-high speed of 16,000 rpm for 20 min, the supernatant was collected, diluted with mobile phase to a certain volume, the concentration of the drug in the upper layer of the suspension was measured by HPLC method, and the total amount of drug in the upper layer of the suspension (C) was calculated.

The drug in the precipitates after low-speed centrifugation and the drug in the supernatant after the super-high centrifugation are the drugs that were not encapsulated.

The encapsulation efficiency and the drug loading were calculated.

Encapsulation Efficiency=$(A-B-C)/A\times100\%$

Drug Loading=$EE\times W_{drug}/(W_{drug}+W_{albumin})$

EE is Encapsulation Efficiency. $W_{drug}$ is the total amount of drug that is fed during the preparation process of the particles. $W_{albumin}$ is the total amount of albumin that is fed during the preparation process of the particles albumin.

TABLE 1

The drug loading and encapsulation efficiency of the albumin particles

|   | example 1 | example 2 | example 3 | example 4 | example 5 | example 6 | example 3b | example 5b |
|---|---|---|---|---|---|---|---|---|
| encapsulation efficiency (%) | 99.2% | 98.6% | 94.5% | 96.8% | 94.4% | 92.3% | 98.7 | 99.2% |
| drug loading (%) | 33.1% | 24.6% | 23.6% | 24.2% | 23.6% | 21.4% | 24.7% | 24.8% |

Assay 2—Measurement of Particle Size of Albumin Particles

Albumin particles of examples 1~6 were provided, added with water to form suspensions, the suspensions were put in a laser particle size analyzer to measure the particle sizes of the particles. The results are as follows:

TABLE 2 particle sizes of albumin particles

|   | example 1 | example 2 | example 3 | example 4 | example 5 | example 6 | example 3b | example 5b |
|---|---|---|---|---|---|---|---|---|
| Particle size (nm) | 186 | 173 | 192 | 204 | 193 | 153 | 195 | 202 |

According to table 2, protein particles with poorly water-soluble drug encapsulated therein can be obtained by methods of example 1~6, for example protein nanoparticle with poorly water-soluble drug encapsulated therein having particle sizes from 153 nm to 204 nm were obtained.

Assay 3—Measurement of Stability of Paclitaxel Albumin Particles

Figure 2:
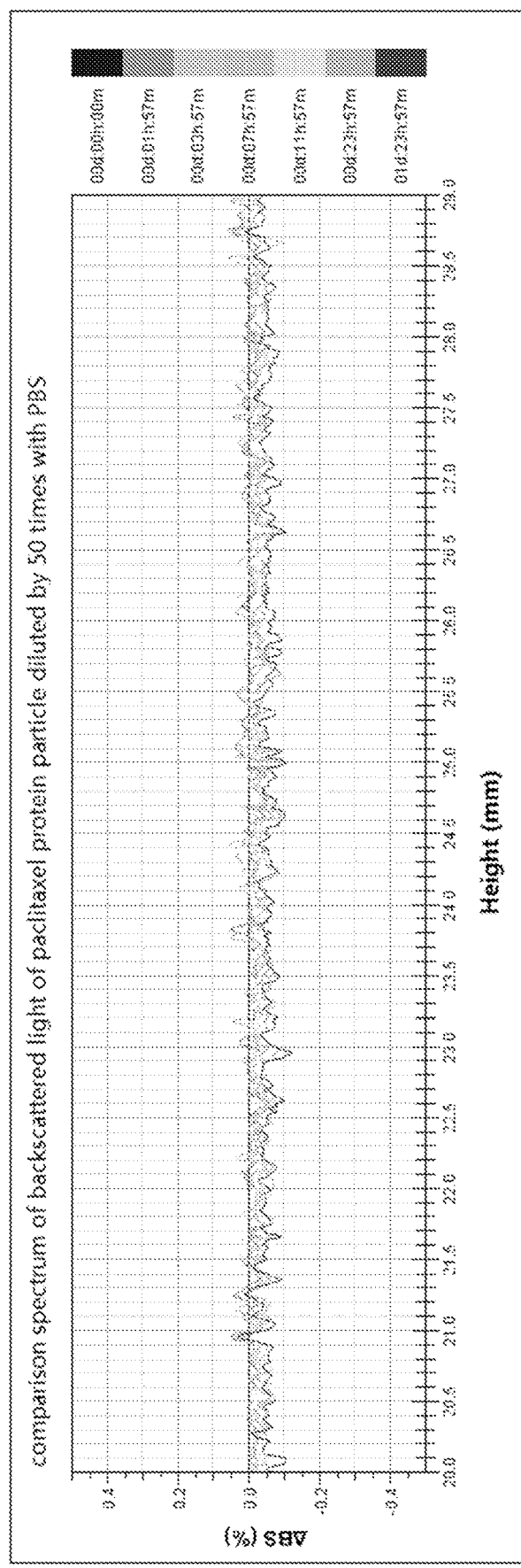
FIG. 2 depicts curves reflecting intensity variation of backscattered light of paclitaxel protein particles diluted by 50 times with PBS.
Figure 3:
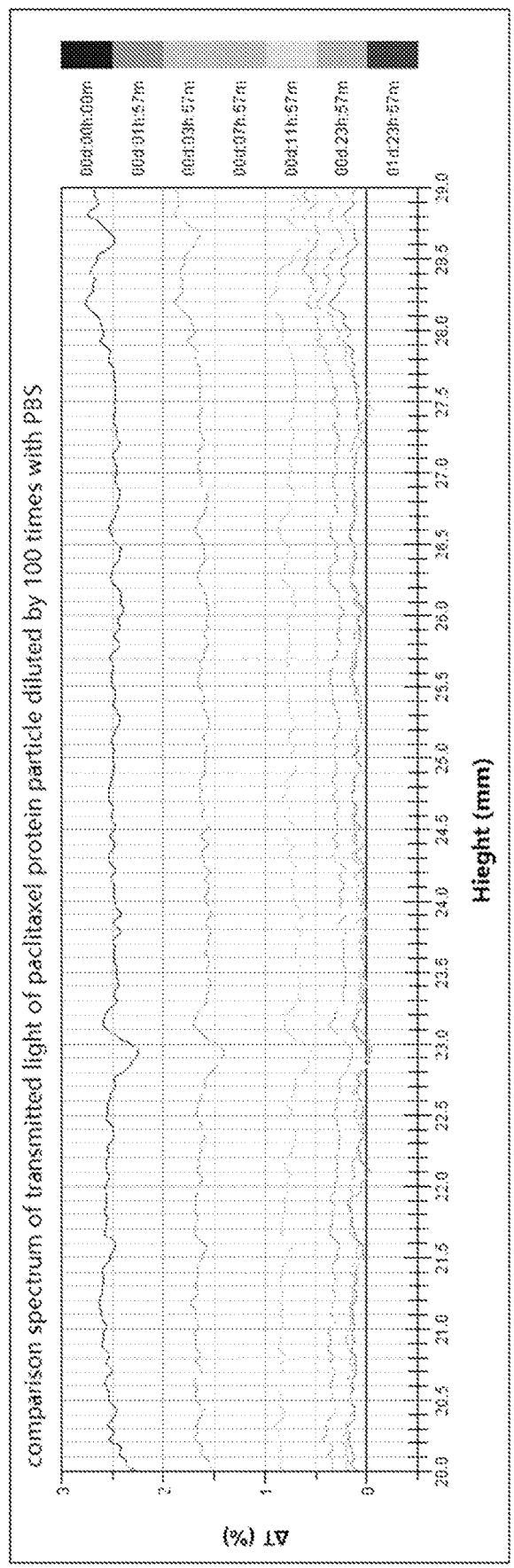
FIG. 3 depicts curves reflecting intensity variation of transmitted light of paclitaxel protein particles diluted by 100 times with PBS.
Figure 4:
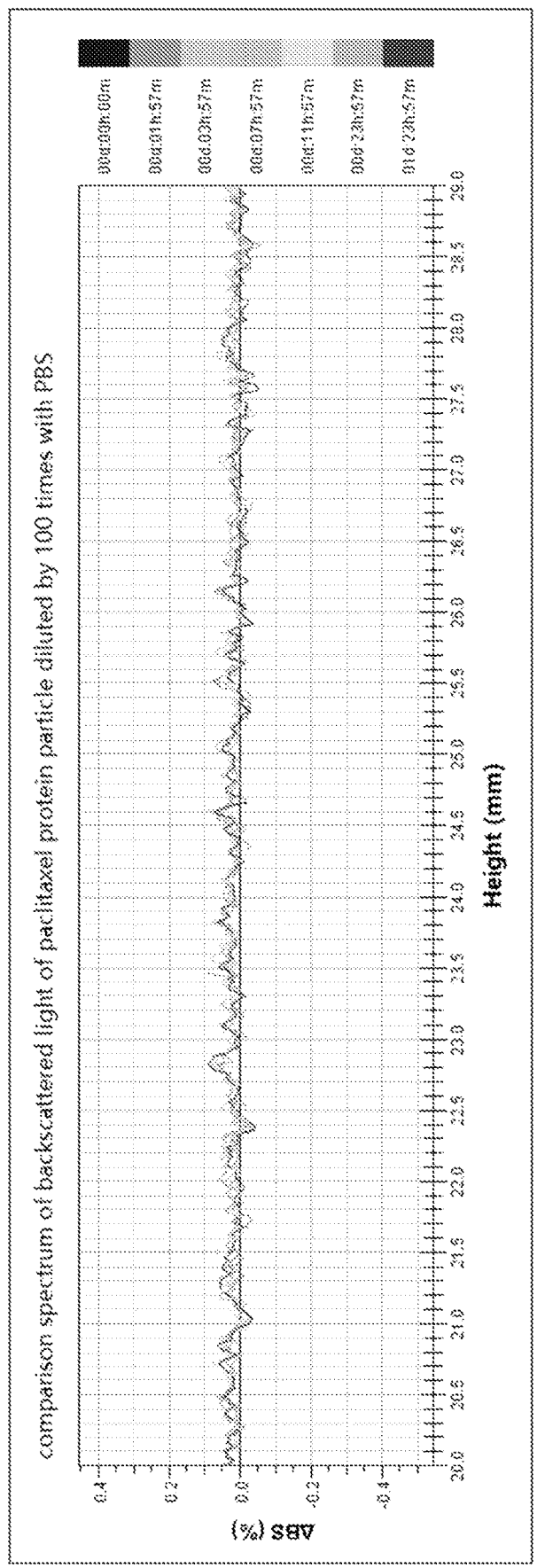
FIG. 4 depicts curves reflecting intensity variation of backscattered light of paclitaxel protein particles diluted by 100 times with PBS.
Figure 5:
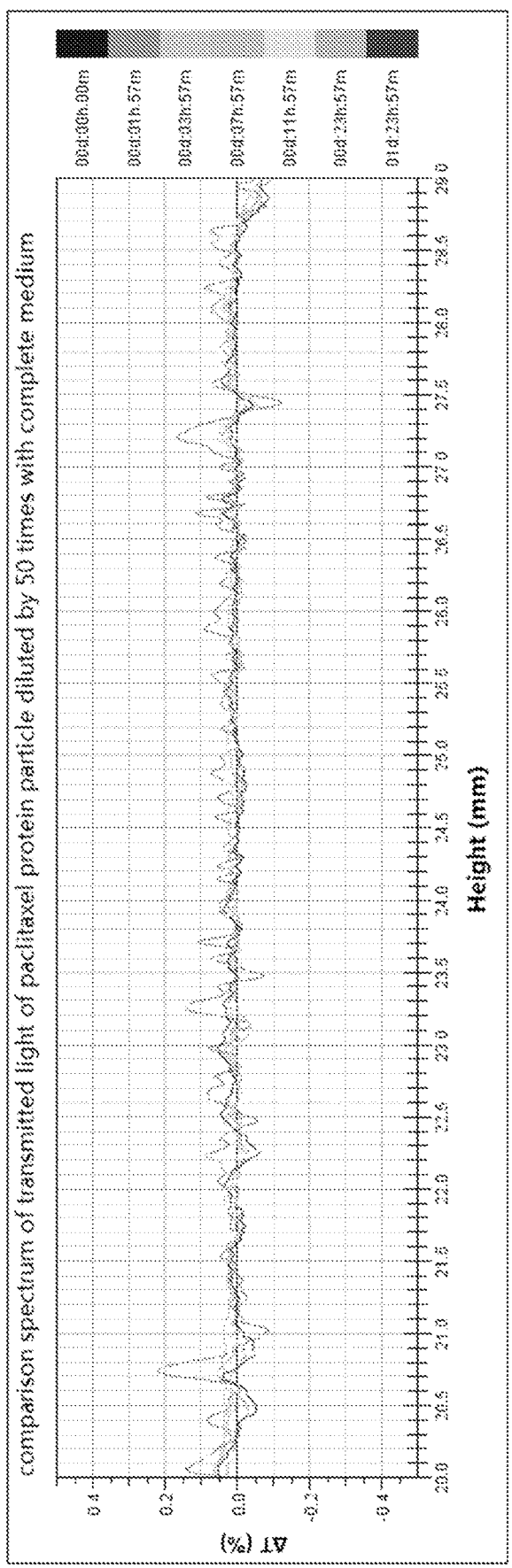
FIG. 5 depicts curves reflecting intensity variation of transmitted light of paclitaxel protein particles diluted by 50 times with complete medium.
Figure 6:
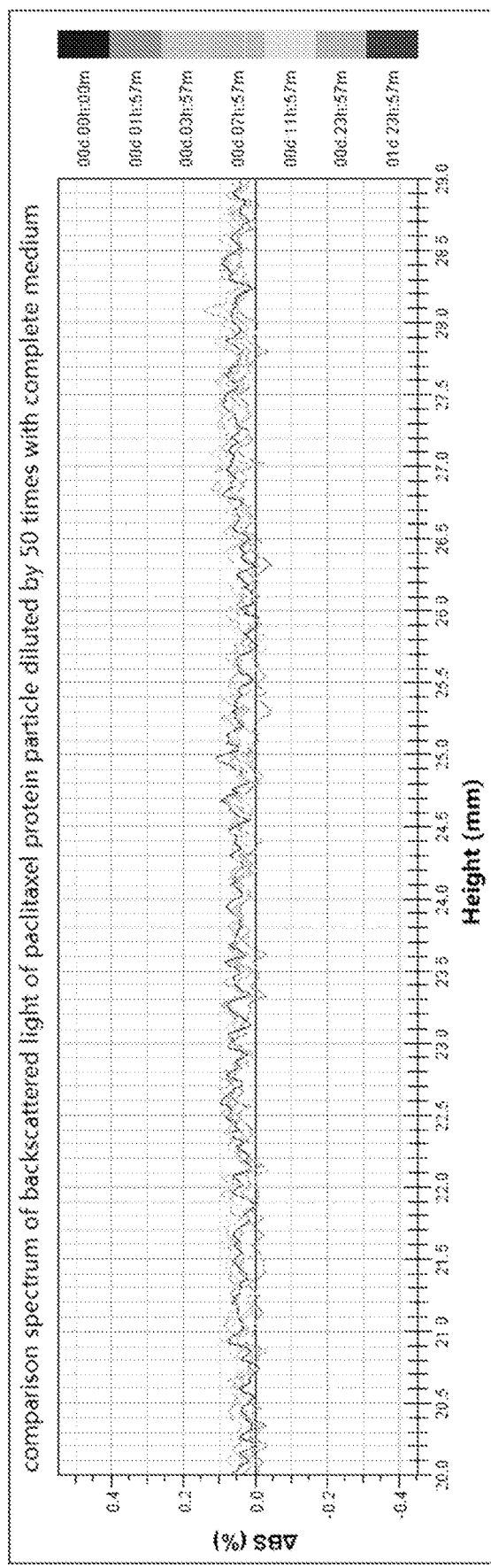
FIG. 6 depicts curves reflecting intensity variation of backscattered light of paclitaxel protein particles diluted by 50 times with complete medium.
Figure 7:
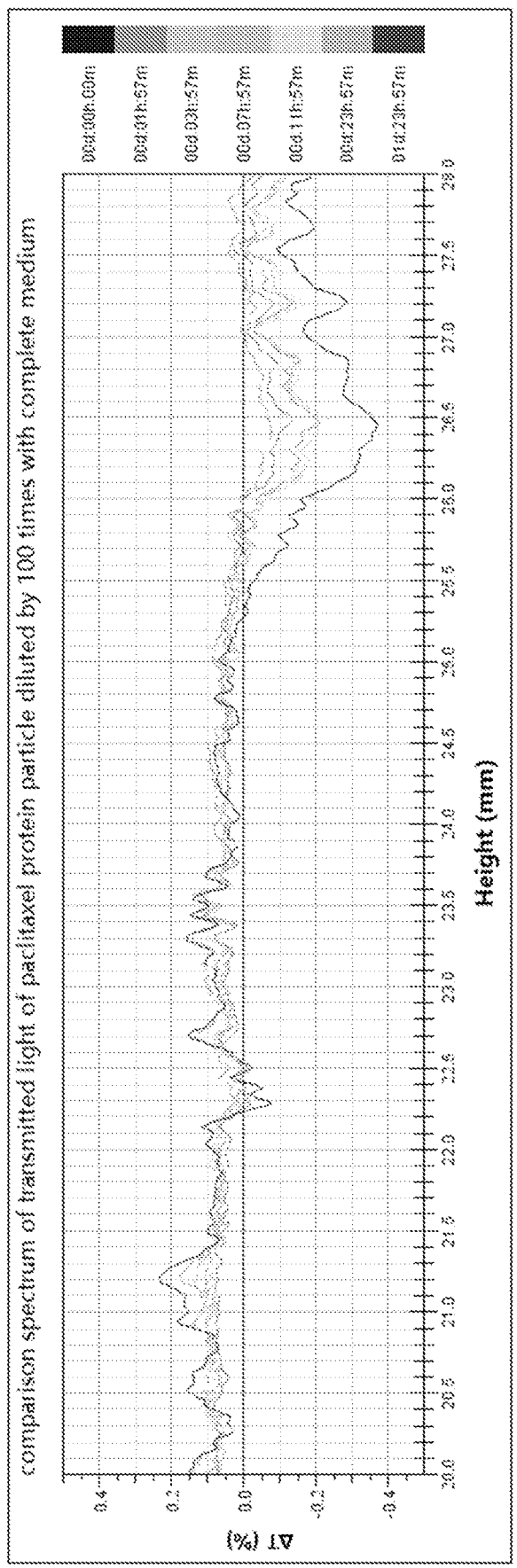
FIG. 7 depicts curves reflecting intensity variation of transmitted light of paclitaxel protein particles diluted by 100 times with complete medium.
Figure 8:
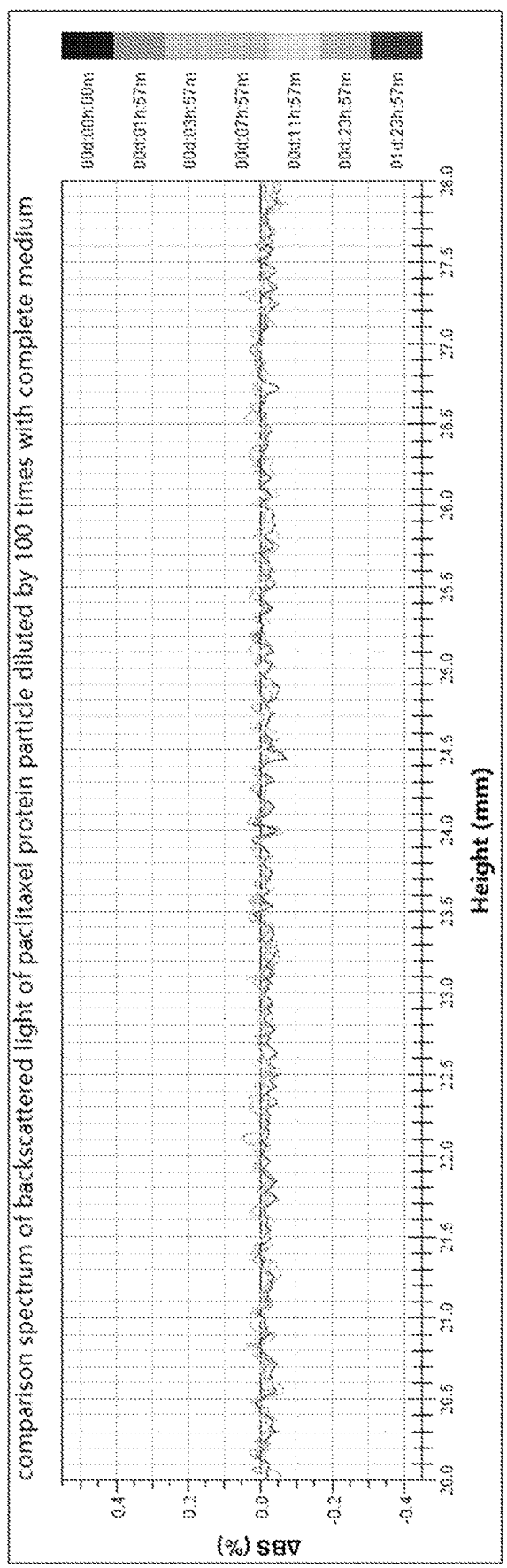
FIG. 8 depicts curves reflecting intensity variation of backscattered light of paclitaxel protein particles diluted by 100 times with complete medium.

The paclitaxel albumin particles of Example 1 were provided and diluted with phosphate buffer solution (PBS) and minimum essential medium (MEM) containing fetal calf serum respectively by 50 times and by 100 times. The stability of the stock solution and the diluted solutions were measured by a stability meter. The results are shown in FIGS. 1~8. FIG. 1 depicts curves reflecting intensity variation of transmitted light of paclitaxel protein particle diluted by 50 times with PBS. FIG. 2 depicts curves reflecting intensity variation of backscattered light of paclitaxel protein particles diluted by 50 times with PBS. FIG. 3 depicts curves reflecting intensity variation of transmitted light of paclitaxel protein particles diluted by 100 times with PBS. FIG. 4 depicts curves reflecting intensity variation of backscattered light of paclitaxel protein particles diluted by 100 times with PBS. FIG. 5 depicts curves reflecting intensity variation of transmitted light of paclitaxel protein particles diluted by 50 times with complete medium. FIG. 6 depicts curves reflecting intensity variation of backscattered light of paclitaxel protein particles diluted by 50 times with complete medium. FIG. 7 depicts curves reflecting intensity variation of transmitted light of paclitaxel protein particles diluted by 100 times with complete medium. FIG. 8 depicts curves reflecting intensity variation of backscattered light of paclitaxel protein particles diluted by 100 times with complete medium. The results indicate that the intensity variation of both transmitted light and backscattered light of paclitaxel albumin particles diluted by various medium at 37° C. are no more than 3%, which indicates the paclitaxel protein particles have good stability.

Finally, it should be noted that the above examples are only for illustrating the embodiments of the present disclosure rather than limiting them; although the present disclosure is described in detail with reference to the preferred examples, those of ordinary skill in the art should understand: the detailed examples can be modified and some of the technical features can be equivalently substituted as long as they do not depart from the spirit of the embodiments of the present disclosure. These modifications and substitutions should all be covered within the scope of the claims claimed by the disclosure.

The invention claimed is:

1. A method for preparing a protein particle with a poorly water-soluble drug encapsulated therein, comprising the following steps:
   i) dissolving a poorly water-soluble drug and a liquid solubilizer into a first solvent, wherein said first solvent comprises one of more selected from the group consisting of ethanol, methanol, diethyl ether, dichloromethane, and chloroform;
   ii) partially or fully removing said first solvent from the product of step i) to form a liquid complex comprising the poorly water-soluble drug and the liquid solubilizer;
   iii) mixing the product of step ii) with a protein, wherein said protein is albumin;
   iv) dispersing the product of step iii) in a second solvent, wherein said second solvent is selected from the group consisting of water, phosphate buffer saline buffer solution and citric acid buffer solution;
   wherein said poorly water-soluble drug has solubility as follows: 1 gram of said poorly water-soluble drug is incapable of being completely dissolved in 30 ml or more of water.

2. The method according to claim 1, wherein said liquid solubilizer comprises one of more selected from the group consisting of propanol, liquid polyethylene glycol, polysorbates, sorbitan esters and glycerol.

3. The method according to claim 1, wherein step ii) comprises: partially or fully removing said first good solvent from the product of step i) by one or more operations selected from the group consisting of rotating evaporation, heating and vacuum pumping.

4. The method according to claim 1, wherein in step iii), said protein is in powder form.

5. The method according to claim 1, wherein the albumin comprises one or more selected from the group consisting of recombinant albumin and natural albumin.

6. The method according to claim 1, wherein step iv) comprises: dispersing the product of step iii) in the second solvent by one or more operations selected from the group consisting of stirring, shearing, ultrasonic treatment, homogenizing, and grinding.

7. The method according to claim 1, further comprising removing the liquid solubilizer from the product of step iv).

8. The method according to claim 1, further comprising separating an albumin particle from the product of step iv).

9. The method according to claim 1, wherein said poorly water-soluble drug comprises one or more selected from the group consisting of paclitaxel, docetaxel, camptothecin, hydroxycamptothecin, rapamycin, doxorubicin, itraconazole and nimodipine.

10. The method according to claim 1, wherein said liquid solubilizer is selected from the group consisting of liquid polyethylene glycol, and polysorbates.

11. The method according to claim 1, wherein said protein particle with a poorly water-soluble drug encapsulated therein has an average particle size of 100 nm-1000 nm.

12. The method according to claim 1, wherein said albumin comprises one or more selected from the group consisting of natural albumin and modified albumin.

13. A protein particle with a poorly water-soluble drug encapsulated therein, prepared by the method according to claim 1.

* * * * *

UNITED STATES PATENT AND TRADEMARK OFFICE
CERTIFICATE OF CORRECTION

PATENT NO. : 11,260,031 B2
APPLICATION NO. : 16/608638
DATED : March 1, 2022
INVENTOR(S) : Zhiping Li et al.

It is certified that error appears in the above-identified patent and that said Letters Patent is hereby corrected as shown below:

In the Claims

Column 12, Claim 1, Line 39, delete "of" and replace with --or--.

Column 12, Claim 1, Line 41, delete ",".

Column 12, Claim 3, Line 60, delete "good".

Signed and Sealed this
Twenty-eighth Day of June, 2022

Katherine Kelly Vidal
*Director of the United States Patent and Trademark Office*